United States Patent [19]

Yamatsu et al.

[11] Patent Number: 4,917,829

[45] Date of Patent: * Apr. 17, 1990

[54] 3,7,11,15-TETRAMETHYL-2,4,6,10,14,-HEXADECAPENTAENDIC ACID

[75] Inventors: Isao Yamatsu, Kawaguchi; Yuichi Inai, Tokyo; Shinya Abe, Kawagoe; Takeshi Suzuki, Abiko; Yoshikazu Suzuki, Ichinomiya; Osamu Tagaya, Gifu; Kouichi Suzuki, Kakamigahara; Koichi Abe, Fuchu; Kouji Yamada, Tokyo, all of Japan

[73] Assignee: Eisai Co., Ltd., Tokyo, Japan

[ * ] Notice: The portion of the term of this patent subsequent to Apr. 7, 2004 has been disclaimed.

[21] Appl. No.: 865,934

[22] Filed: May 16, 1986

Related U.S. Application Data

[60] Continuation of Ser. No. 535,480, Sep. 26, 1983, abandoned, which is a division of Ser. No. 249,245, Mar. 30, 1981, abandoned.

[30] Foreign Application Priority Data

Apr. 7, 1980 [JP] Japan .................................. 55-44558

[51] Int. Cl.$^4$ ....................... C07C 57/03; A61K 31/20
[52] U.S. Cl. .................................................... 260/413
[58] Field of Search ....................... 260/413 C, 413 R; 514/560

[56] References Cited

U.S. PATENT DOCUMENTS

| 4,116,955 | 9/1978 | Ichikawa et al. | 260/192 |
| 4,147,708 | 4/1979 | Manchand | 260/413 L |
| 4,346,109 | 8/1982 | Yamatsu et al. | 424/318 |

FOREIGN PATENT DOCUMENTS 2073750  10/1981  United Kingdom ................ 260/413

OTHER PUBLICATIONS

Bollag, Werner, *European Journal of Cancer*, vol. 10, 1974, Pergamon Press, Great Britain, pp. 731–737.

Davis, J. B. et al., *Journal Chemical Society*, (London), (C), 1966, pp. 2154–2165.

*Primary Examiner*—Charles F. Warren
*Attorney, Agent, or Firm*—Flynn, Thiel, Boutell & Tanis

[57] ABSTRACT

A novel compound, 3,7,11,15-tetramethyl-2,4,6,10,14-hexadecapentaenoic acid, and a salt thereof are disclosed together with a number of different processes for the preparation of the compound. The uses of the novel compound as an anticancer agent are also disclosed.

3 Claims, No Drawings

3,7,11,15-TETRAMETHYL-2,4,6,10,14,-HEXADECAPENTAENDIC ACID

This is a continuation of Ser. No. 535,480 filed 9.26.83 abandoned, which is a division of application Ser. No. 249 245, filed Mar. 30, 1981 abandoned.

This invention relates to a novel compound of 3,7,11,15-tetramethyl-2,4,6,10,14-hexadecapentaenoic acid having the general formula (I) as follows and a pharmaceutically acceptable

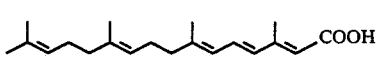  (I)

salt thereof. This invention further relates to processes for the preparation of the same and an anticancer agent comprising the same.

W. Bollag, et al. reported in Europ. J. Cancer, vol. 10, p 731(1974) that retinoides such as ethyl 9-(2,3,6-trimethyl-4-methoxyphenyl)-3,7-dimethyl-2,4,6,8-nonatetraenoate have anticancer activity. These retinoide compounds, however, are highly toxic, and further have problems such as causing hypervitaminosis of Vitamin A when administered.

The compound of the above-mentioned general formula (I) provided by the present invention shows the anticancer activity, causes substantially no hypervitaminosis of Vitamin A, and is low in other toxicities.

The compound of the present invention can be prepared by the following processes.

Process A

This process comprises:
(1) reacting a compound of the general formula (II):

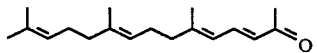  (II)

and a Wittig reagent derived from a compound of the general formula (III):

$X-CH_2-CO_2R_1$   (III)

in which X represents a halogen atom, and $R_1$ represents a lower alkyl group, to obtain a compound of the general formula (IV):

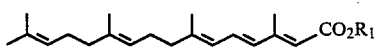  (IV)

in which $R_1$ has the same meaning as defined above; and (2) hydrolyzing the so obtained commpound of the general formula (IV) in the presence of a base to prepare the compound of the general formula (I).

Examples of the Wittig reagents employed in the above-described (1) stage and derived from a compound of the general formula (III) include phosphoric compounds produced by the reaction between the compound of the general formula (III) and triphenylphosphine, phenyldialkoxyphosphine, trialkylphosphite, or the like. The preparation of the reagent and the Wittig reaction employing the reagent are carried out by the conventional methods such as the method given by Wadworth, et al. in J. Am. Chem. Soc., vol. 83, p. 1733 (1961), the method given by Greenwald, et al. in J. Org. Chem., vol. 28, p. 1128 (1963), and the method given by Horner, et al. in Ber. vol. 95, p. 581 (1962).

In the above-mentioned (2) stage, the hydrolysis is carried out in the presence of a base generally employed for hydrolysis of carboxylic acid esters, such as sodium hydroxide and potassium hydroxide.

Process B

This process comprises:
(1) reacting a compound of the general formula (V):

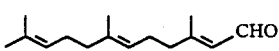  (V)

and a Wittig reagent derived from a compound of the general formula (VI):

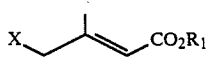  (VI)

in which X represents a halogen atom, and $R_1$ represents a lower alkyl group, to obtain a compound of the general formula (IV); and (2) hydrolyzing the so obtained compound of the general formula (IV) in the presence of a base to prepare the compound of the general formula (I).

Each of the above-described stages (1) and (2) can be carried out in the same manner as in Process A.

Process C

This process comprises:
(1) reacting a compound of the general formula (VII):

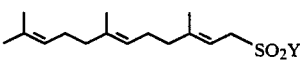  (VII)

in which Y represents a lower alkyl group or an aryl group, and a compound of the general formula (VI), to obtain a compound of the general formula (VIII):

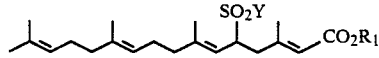  (VIII)

in which Y and $R_1$ have the same meanings as defined above; and (2) subjecting the so obtained compound of the general formula (VIII) to a desulfination reaction and then hydrolysis of the ester in the presence of a base to prepare the compound of the general formula (I).

The stage (1) is carried out in the presence of a base. Examples of the bases include n-butyllithium and phenyllithium. Examples of the reaction solvents include tetrahydrofuran, diethyl ether and 1,2-dimethoxyethane. The reaction is generally carried out at a temperature lower than room temperature.

The stage (2) can be carried out in the same manner as the stage (2) of the aforementioned Process A.

Examples of the substituents provided to the general formulae (III), (IV), (VI), (VII) and (VIII) are as follows:

halogen atoms such as chlorine, bromine and iodine for the substituent X; lower alkyl groups such as methyl, ethyl and propyl for the substituent $R_1$: and lower alkyl groups such as methyl, ethyl and propyl, and aryl groups such as phenyl and p-tolyl for the substituent Y.

Examples of the salts of the compound of the general formula (I) include its sodium salt and its potassium salt.

The results of the pharmacological tests and toxicity tests on the compound of the present invention are set forth below.

Pharmacological Tests (Anticancer Activity)

(1) Experimental procedure

A mouse (ICR, female, 60 days age) was shaved at the back of the neck (5 cm$^2$). 7,12-Dimethylbenzo-[2]-anthracene was dissolved in acetone to give 75 mg./100 ml. solution. The so prepared solution was applied to the mouse on the 60th aged day and further on the 75th aged day in the amount of 0.2 ml. per a mouse.

Crotonic oil was dissolved in acetone to give 250 mg./100 ml. solution, and the so prepared solution was applied to the mouse in the amount of 0.2 ml. per a mouse, twice a week until the beginning of the treatment. When 3-7 papillomata (diameter of 3-8 mm. for each, and total diameter of 30-60 mm.) were produced per a mouse, the treatment was started.

The test compound was dissolved in groundnut oil to give 20 mg./ml. solution, and administered orally to the mouse. The solution was administered 10 times for 14 days (once a day), and the diameters of the papillomata were measured on the 14th day to determine the total diameter for each mouse.

(2) Test compound 3,7,11,15-Tetramethyl-2,4,6,10,14-hexadecapentaenoic acid (the compound according to the present invention)

Ethyl-9-(2,3,6-trimethyl-4-methoxyphenyl)-3,7-dimethyl-2,4,6,8-nonatetraenoate (control compound)

As seen from the above Table 1, the compound of the invention is effective against the papilloma.

Toxicity Tests (1) Experimental procedure

The test compound was administered repeatedly to a group of 6 mice (ICR strain, female) for 14 days. The amount of the administration was 40 mg./Kg./day, 200 mg./Kg./day, and 400 mg./Kg./day for the compound of the present invention, and 200 mg./Kg./day for the control compound. In the course of the administration, increase or decrease of the weight of the mouse, occurrence of death, etc. were observed.

(2) Test compound

The compounds described in the pharmacological tests (anticancer activity) were employed.

(3) Experimental results (a) Increase and decrease of the weight The results are set forth in Table 2.

(b) Death

All mice treated with the control compound in the amount of 200 mg./Kg./day died by the 8th day, and no death was observed on the mice treated with the compound of the present invention.

(c) Falling-out of hair

Falling-out of hair was observed by the 6th day on every mouse treated with the control compound in the amount of 200 mg./Kg./day, and no falling-out of hair was observed on the mouse treated with the compound of the present invention.

(d) Cyanosis

Cyanosis was observed by the 7th day on every mouse treated with the control compound in the amount of 200 mg./Kg./day, and no cyanosis was observed on the mouse treated with the compound of the present invention.

TABLE 2

| Test Compound | Amount of Administration (mg./Kg./day) | Average of Weight (g) | | | | | | | |
|---|---|---|---|---|---|---|---|---|---|
| | | 0 | 2 | 4 | 6 | 8 | 10 | 12 | 14 |
| No administration | | 20.5 | 22.3 | 22.1 | 22.1 | 22.0 | 22.3 | 23.0 | 23.6 |
| Compound | 40 | 20.9 | 22.4 | 22.2 | 22.6 | 23.1 | 23.0 | 22.6 | 24.0 |
| of | 200 | 21.4 | 21.7 | 20.0 | 21.9 | 22.8 | 22.9 | 23.3 | 24.1 |
| the invention | 400 | 25.4 | 26.5 | 28.0 | 26.4 | 26.3 | 26.6 | 26.3 | 27.0 |
| Control | 40 | 21.2 | 21.8 | 20.7 | 20.5 | 19.6 | 18.8 | 17.3 | 15.6 |
| Compound | 200 | 21.5 | 18.9 | 15.0 | 13.3 | 11.5 | — (death) | — (death) | — (death) |

(3) The results are set forth in Table 1.

TABLE 1

| Test Compound | Number of mice | Papilloma (total diameter/mouse) | | Ratio of Increase or Decrease |
|---|---|---|---|---|
| | | Mean Value (0th day) | Mean Value (14th day) | |
| Groundnut oil only | 3 | 33.9 mm | 39.7 mm | +17.1% |
| Compound of the invention (200 mg./Kg./day) | 5 | 37.5 mm | 21.3 mm | −43.2% |
| Control compound (40 mg./Kg./day) | 3 | 58.1 mm | 32.7 mm | −43.7% |

Among the subjects in the toxicity tests, the falling-out of hair and the weight change are known to indicate the hypervitaminosis of Vitamin A. Since the falling-out of hair and decrease of the weight were observed at a prominently high level on the group of mice treated with the control compound, it is thought that the hypervitaminosis of Vitamin A occurred. In contrast, there was observed no such problem on the group of mice treated with the compound of the present invention.

In view of the pharmacological test results and the toxicity tests results hereinbefore described, the compound of the present invention is considered to be of high safety and to be of value as an anticancer agent.

Therefore, the compound of the present invention can be employed for the treatment of cancer and precancerous conditions.

For the applications as the anticancer agent and the therapeutic agent for treatment of skin disease with keratinization, the compound of the present invention is administered orally in the form of powder, granule, pellet, hard capsule, etc., or parenterally in the form of ointment, suppository, injection solution, etc. The dosage is generally 40 mg.—4 g./day for adult. If the compound of the present invention is employed in the form of an external preparation, the dosage can be varied depending on the conditions of the disease. The compound of the present invention can be combined with a generally employable carrier for the medical use in the conventional manner to give the preparations described above.

The processes for the preparation of the compound of the present invention are illustrated by the following examples, but these examples are not intended to restrict the present invention.

EXAMPLE 1

To a suspension of 5.0 g of 55% sodium hydride (oily) in 60 ml. of n-hexane was added 28.6 g. of triethyl phosphonoacetate. The mixture was then heated under reflux, and 20 g. of 6,10,14-trimethyl-3,5,9,13-pentadecatetraen-2-one was added dropwise to the mixture under stirring. After 30 minutes, the reaction liquid was poured into 200 ml. of water, and then 500 ml. of n-hexane was added for extraction. The n-hexane phase was separated, washed with two 100 ml. portions of a mixture of methanol and water (2:1), and concentrated. The so obtained concentrate was purified by the silica gel column chromatography to give 18 g. of ethyl 3,7,11,15-tetramethyl-2,4,6,10,14-hexadecapentaenoate.

To 10 g. of the ethyl 3,7,11,15-tetramethyl-2,4,6,10,14-hexadecapentaenoate obtained in the above was added a solution of 3.9 g. of potassium hydroxide in 30 ml. of isopropyl alcohol, and the mixture was stirred at 50° C. for 1 hour. The reaction liquid was then poured into ice-water, made acidic by addition of hydrochloric acid, and extracted with 100 ml. of ethyl ether. The ether phase was washed with water, dried over magnesium sulfate, and concentrated to give 9.0 g. of an oil. The oil was dissolved in 50 ml. of n-hexane and crystallized at −20° C. to give 4.0 g. of 3,7,11,15-tetramethyl-2,4,6,10,14-hexadecapentaenoic acid in the form of pale yellow needles.

M.p.: 78.4° C.
Mass spectrum (m/e): 302 (M+)
Infrared absorption spectrum (cm$^{-1}$, KBr tablet): 3450, 2900, 1680, 1595
NMR spectrum (8, CDCl$_3$): 1.61 (6H, s), 1.68 (3H, s), 1.86 (3H, s), 1.92–2.24 (8H, b), 2.35 (3H, s), 5.10 (2H, b), 5.76 (1H, bs), 5.98 (1H, d, J=11 Hz), 6.20 (1H, d, J=15 Hz), 6.90 (1H, dd, J=11 Hz, 15 Hz), 11.63 (1H, b)
Ultraviolet absorption spectrum: $\lambda_{max}^{methanol}$ 304 nm

EXAMPLE 2

To a suspension of 4.8 g of sodium ethoxide in 100 ml. of n-hexane was added 18 g. of diethyl 3-ethoxycarbonyl-2-methyl-2-propenylphosphonate. To the mixture was added 10 g. of 3,7,11-trimethyl-2,6,10-dodecatrien-1-al under stirring at room temperature. After 1 hour, the reaction liquid was poured into 50 ml. of water, and the n-hexane phase was separated. The n-hexane phase was washed with two 50 ml. portions of a mixture of methanol and water (2:1), and concentrated. The so obtained concentrate was purified by the silica gel column chromatography to give 14.5 g. of ethyl 3,7,11,15-tetramethyl-2,4,6,10,14-hexadecapentaenoate.

10 g. of the ethylester obtained in the above was hydrolyzed in the same manner as in Example 1 to give 3.5 g. of 3,7,11,15-trimethyl-2,4,6,10,14-hexadecapentaenoic acid in the form of yellow needles.

The so obtained product was identified in the same manner as in Example 1, namely, by m.p., mass spectrum, NMR spectrum, infrared absorption spectrum, and ultraviolet absorption spectrum.

EXAMPLE 3

In 100 ml. of tetrahydrofuran was dissolved 10 g. of 1-p-tolylsulfonyl-3,7,11-trimethyl-2,6,10-dodecatriene, and the solution was chilled to −50° C. To the solution was added dropwise 18.5 ml. of 15% n-butyllithium-n-hexane solution under stirring and in a stream of nitrogen, maintaining the temperature of the solution at −50° C. Then, 300 ml. of tetrahydrofuran solution containing 5.7 g. of ethyl 4-bromo-3-methyl-2-butenate was added dropwise to the so produced solution. After 30 minutes, 100 ml. of 10% aqueous ammonium chloride solution was added, and subsequently the mixture was treated to reach room temperature. The mixture was then extracted with two 200 ml. portions of n-hexane. The n-hexane phase was washed with three 100 ml. portions of water, dried over magnesium sulfate, and concentrated to give 13 g. of ethyl 3,7,11,15-tetramethyl-5-p-tolylsulfonyl-2,6,10,14- hexadecatetraenoate.

To 10 g. of the ethylester obtained in the above was added a solution of 4.6 g. of potassium hydroxide in 50 ml. of isopropyl alcohol, and the mixture was stirred at 50° C. for 3 hours. The reaction liquid was then poured into ice-water, made acidic by addition of hydrochloric acid, and extracted with 100 ml. of ethyl ether. The ethyl ether phase was washed with water, dried over magnesium sulfate, and concentrated to give 6 g. of an oil. The oil was dissolved in 30 ml. of n-hexane and crystallized at −20° C. to give 1.8 g. of 3,7,11,15-tetramethyl-2,4,6,10,14-hexadecapentaenoic acid in the form of pale yellow needles.

The so obtained product was identified in the same manner as in Example 1, namely, by m.p., mass spectrum, NMR spectrum, infrared absorption spectrum, and ultraviolet absorption spectrum.

EXAMPLE 4

| Pellet | |
| --- | --- |
| 3,7,11,15-Tetramethyl-2,4,6,10,14-hexadecapentaenoic acid | 50 g. |
| Silicic acid anhydride | 30 g. |
| Crystalline cellulose | 50 g. |
| Corn starch | 36 g. |
| Hydroxypropylcellulose | 10 g. |
| Magnesium stearate | 4 g. |

The above composition was processed in the conventional manner to give a pellet (180 mg. for a pellet).

I claim:
1. 3,7,11,15-Tetramethyl-2,4,6,10,14-hexadecapentaenoic acid of the formula (I):

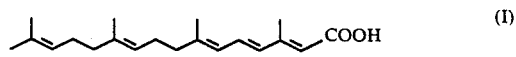

or a pharmaceutically acceptable salt thereof.

2. A method of treating precancerous skin conditions which comprises administering to a subject requiring such treatment a therapeutically effective amount of a pharmaceutical composition comprising 3,7,11,15-tetramethyl-2,4,6,10,14-hexadecapentaenoic acid of the formula (I):
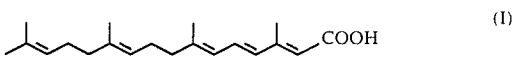
or a pharmaceutically acceptable salt theeof, and a pharmaceutical carrier.
3. A method as claimed in claim 2, in which said composition is administered orally or parenterally and the formula (I) compound is administered in a dosage of from 40 mg to 4 g, per day.
* * * * *